US006499487B1

(12) United States Patent
McKenzie et al.

(10) Patent No.: US 6,499,487 B1
(45) Date of Patent: Dec. 31, 2002

(54) IMPLANTABLE CEREBRAL PROTECTION DEVICE AND METHODS OF USE

(75) Inventors: John McKenzie, San Carlos, CA (US); Sachiko Hattori, Sunnyvale, CA (US)

(73) Assignee: Embol-X, Inc., Mountain View, CA (US)

( * ) Notice: Subject to any disclaimer, the term of this patent is extended or adjusted under 35 U.S.C. 154(b) by 0 days.

(21) Appl. No.: 09/642,570

(22) Filed: Aug. 17, 2000

Related U.S. Application Data

(63) Continuation of application No. 08/996,532, filed on Dec. 23, 1997, now Pat. No. 6,258,120.

(51) Int. Cl.[7] ................................................ A61B 19/00
(52) U.S. Cl. ..................... 128/898; 623/1.31; 623/1.51; 623/902; 604/8; 606/194; 606/200
(58) Field of Search .................. 623/1.31, 1.3, 623/1.36, 1.51, 902, 11.11, 66.1, 23.64, 23.7, 1.39, 903, 1.1, 23.68; 606/108, 191, 194, 195, 200, 198; 604/8; 128/898

(56) References Cited

U.S. PATENT DOCUMENTS

| | | | |
|---|---|---|---|
| 4,382,445 A | 5/1983 | Sommers | 604/8 |
| 4,873,978 A | 10/1989 | Ginsburg | 128/345 |
| 4,969,896 A | 11/1990 | Shors | 623/1 |
| 4,986,831 A | 1/1991 | King et al. | 623/1 |
| 5,053,008 A | 10/1991 | Bajaj | 604/104 |
| 5,375,612 A | 12/1994 | Cottenceau et al. | 128/899 |
| 5,522,881 A | 6/1996 | Lentz | 623/11 |
| 5,545,211 A | 8/1996 | An et al. | 623/1 |
| 5,609,628 A | 3/1997 | Keranen | 623/12 |
| 5,617,878 A | 4/1997 | Taheri | 606/198 |
| 5,674,241 A | 10/1997 | Bley et al. | 623/12 |
| 5,681,345 A | 10/1997 | Euteneuer | 623/12 |
| 5,683,411 A | 11/1997 | Kavteladze et al. | 623/11 |
| 5,759,170 A * | 6/1998 | Peters | 604/4 |
| 5,800,525 A | 9/1998 | Bachinski et al. | 606/200 |
| 5,817,100 A | 10/1998 | Igaki | 623/12 |
| 5,885,238 A * | 3/1999 | Stevens et al. | 604/4 |
| 5,919,224 A | 7/1999 | Thompson et al. | 623/12 |
| 5,951,599 A * | 9/1999 | McCrory | 623/1 |
| 6,048,331 A | 4/2000 | Tsugita et al. | 604/96 |
| 6,139,517 A * | 10/2000 | Macoviak et al. | 604/101.05 |
| 6,235,045 B1 * | 5/2001 | Barbut et al. | 606/200 |

FOREIGN PATENT DOCUMENTS

| | | |
|---|---|---|
| BR | PI 9 301 980 A | 10/1993 |
| DE | 34 17 738 A1 | 11/1985 |
| FR | 2567405 | 1/1986 |
| WO | WO99/16382 | 4/1999 |

OTHER PUBLICATIONS

Katz et al., "Protruding Aortic Atheromas Predict Stroke in Elderly Patients Undergoing Cardiopulmonary Bypass: Experience with Intraoperative Transesophageal Echocardiography", JACC vol. 20, No. 1, Jul. 1992, pp. 70–77.

* cited by examiner

*Primary Examiner*—David J. Isabella
*Assistant Examiner*—Urmi Chattopadhyay
(74) *Attorney, Agent, or Firm*—O'Melveny & Myers LLP

(57) ABSTRACT

Described are devices and methods for diverting emboli away from the carotid arteries in the aorta. The devices are aortic diverters that generally comprise a hollow tube with a substantially cylindrical or conical wall, which is impermeable to emboli and which has open ends that allow blood to enter one end, flow through the tube and exit the other end. Additionally, snowshoe aortic diverters, which are planar rather than cylindrical are also shown. The methods of the invention generally include the steps of providing an aortic diverter carried by an intravascular catheter, introducing the intravascular catheter into the vascular system, advancing the intravascular catheter into the aortic arch to the region of the carotid arteries, and deploying the aortic diverter.

25 Claims, 12 Drawing Sheets

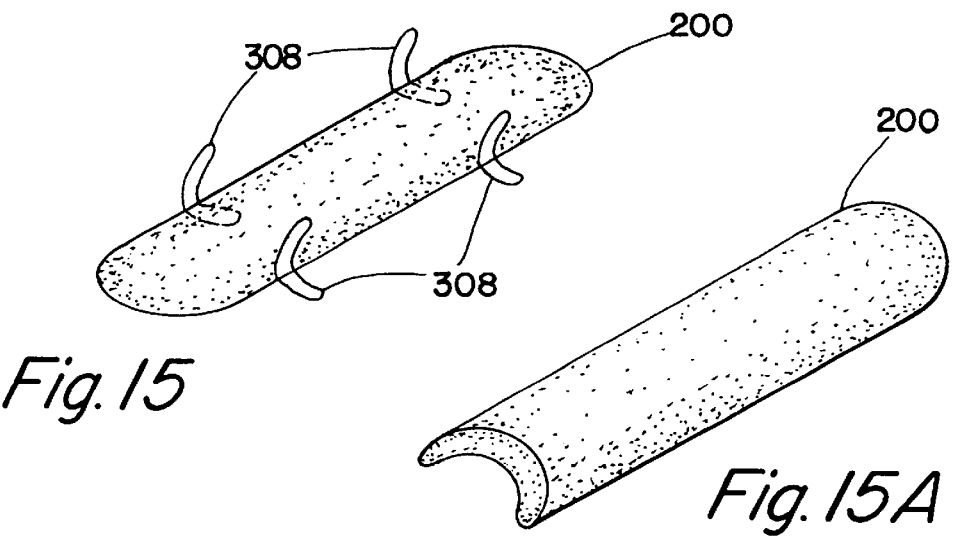
*Fig. 15*
*Fig. 15A*
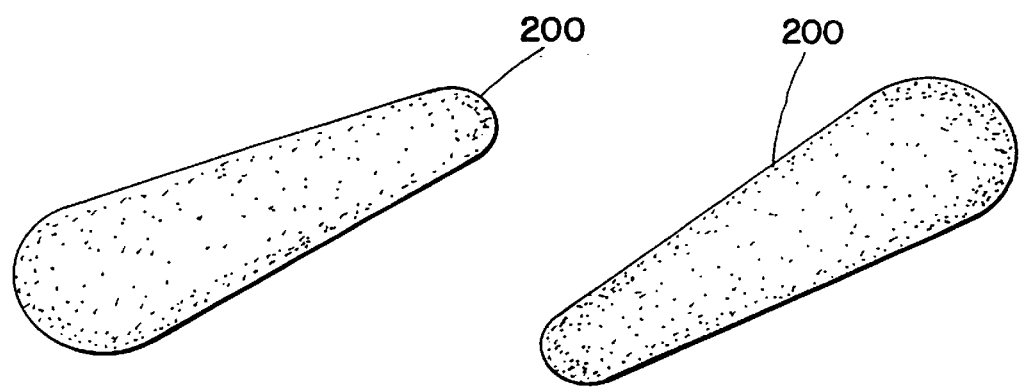
*Fig. 15B*
*Fig. 15C*
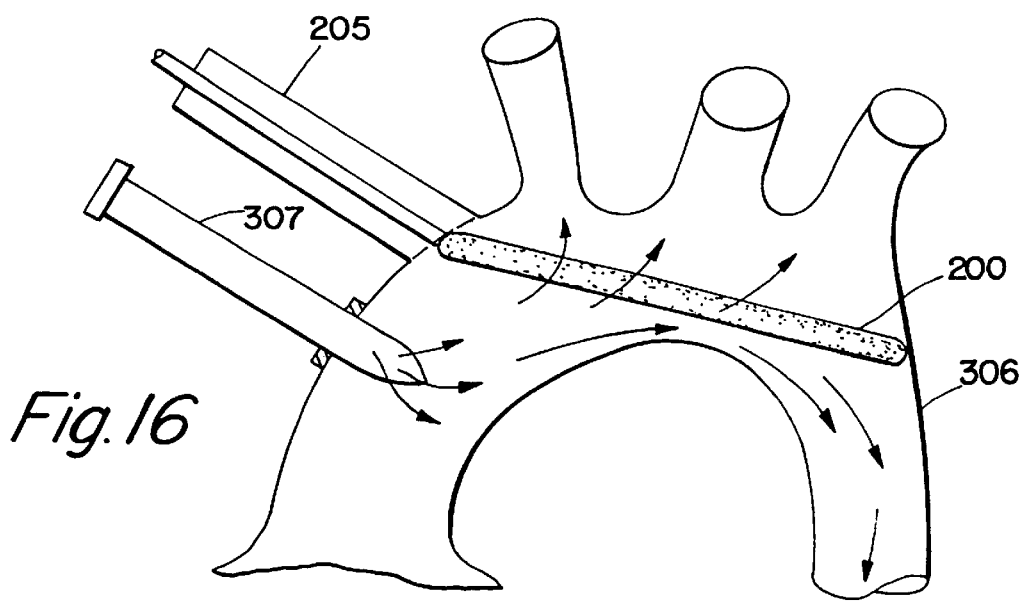
*Fig. 16*

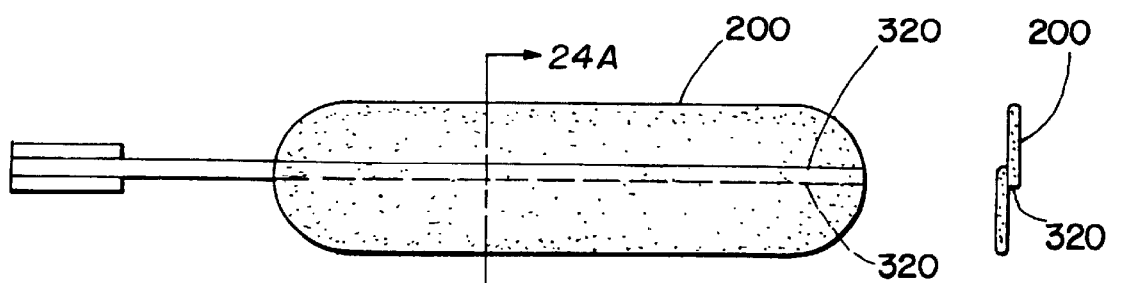
*Fig. 24*   *Fig. 24A*
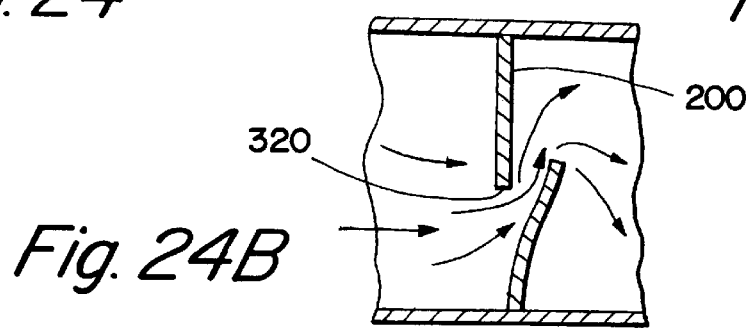
*Fig. 24B*
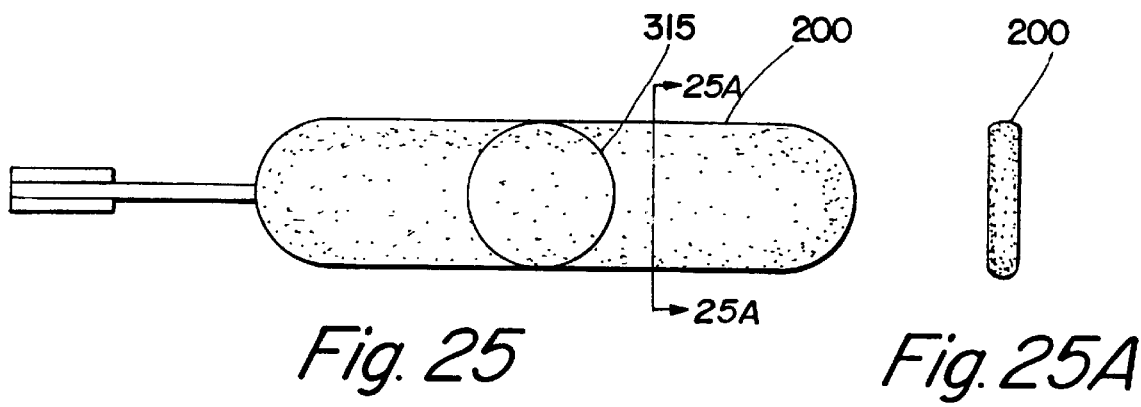
*Fig. 25*   *Fig. 25A*
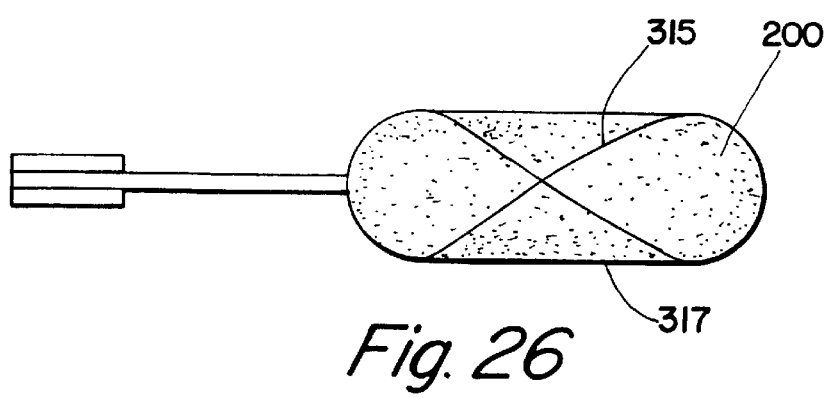
*Fig. 26*

IMPLANTABLE CEREBRAL PROTECTION DEVICE AND METHODS OF USE

This is a continuation of U.S. application Ser. No. 08/996,532, filed Dec. 23, 1997, now U.S. Pat. No. 6,258, 120, the entirety of which is incorporated herein by reference.

FIELD OF THE INVENTION

The present invention relates generally to aortic diverters for temporary or permanent placement in the aorta in order to divert embolic material away from the arteries that carry blood to the brain, i.e., the carotid or cerebral arteries (including the brachiocephalic trunk, the left common carotid, and the left subclavian; Anne R. Agur, Grant's Atlas of Anatomy 52 (9th ed., Williams & Wilkins 1991) (1943) (this and all other references cited herein are expressly incorporated by reference as if set forth in their entirety in this disclosure)). More particularly, the invention relates to aortic diverters placed within the ascending aorta, either temporarily or permanently, such that embolic debris entering the aorta are carried through or past the diverter and past the carotid arteries, thus being diverted away from cerebral blood vessels. The present invention also relates to methods of protecting patients against cerebral embolization by using aortic diverters.

BACKGROUND OF THE INVENTION

Preventing emboli from entering the carotid arteries- (i.e., the brachiocephalic, the left common carotid, and the left subclavian) by way of the aorta reduces the incidence of ischemic stroke. Emboli in the aorta come from several sources. These sources include: 1) aortic atheroma which detaches from the wall of the aorta due to various reasons including incising, clamping, and/or clamp release of the aorta during surgery (see, Barbut et al., "Cerebral Emboli Detected During Bypass Surgery Are Associated With Clamp Removal," Stroke, 25(12):2398–2402 (1994)); 2) thrombus which forms in the right atrium resulting from atrial fibrillation; 3) thrombus which forms on ventricular assist devices; 4) venous thrombus which passes into the left ventricle through a patent foramen ovale or other arteriovenous shunt; and 6) other less common sources.

There are a number of known devices designed to filter blood (see, e.g., Barbut et al., International Application No. PCT/US97/12751, and Barbut et al., U.S. Pat. No. 5,662, 671), but no known devices designed to divert or redirect emboli past the carotid arteries. Using careful surgical techniques, the chance of an embolic event causing harm to the patient by way of cerebral embolization is so low that emboli managing devices have not been considered. Thus, there are no known solutions to minimizing the probability of cerebral embolization; except for reducing the amount of emboli released into the blood stream by careful handling of blood vessels.

On the venous side of the circulatory system, implantable vena cava filters reduce the incidence of pulmonary embolism, but they only trap large emboli, and they have a tendency to become clogged as they accumulate material. For example, Cottenceau et al., U.S. Pat. No. 5,375,612 discloses a blood filter intended for implantation in a blood vessel, typically in the vena cava. This device comprises a zigzagged thread wound on itself and a central strainer section to retain blood clots. Another example is Lefebvre, French Patent No. 2,567,405, which discloses a blood filter for implantation by an endovenous route into the vena cava. The filtering means may consist of a flexible metallic grid, a flexible synthetic or plastic grid, a weave of synthetic filaments, or a non-degradable or possibly biodegradable textile cloth.

There are very few intravascular devices designed for arterial and especially aortic filtration, much less diversion. A filter that functions in arteries must address additional concerns because of the hemodynamic differences between arteries and veins. Arteries are much more flexible and elastic than veins and, in the arteries, blood flow is pulsatile with large pressure variations between systolic and diastolic flow. These pressure variations cause the artery walls to expand and contract. Thus, filters and diverters must be able to expand and contract along with the lumen of the aorta to which they may be anchored.

The problem of preventing emboli from reaching the cerebral vasculature has thus far not been adequately addressed. Therefore, a need exists for new devices and methods to prevent embolic material from entering the carotid/cerebral arteries, while maintaining peripheral blood flow from the heart to the descending aorta.

SUMMARY OF THE INVENTION

The present invention relates to aortic diverters and methods of diverting or redirecting emboli away from the carotid arteries to prevent cerebral embolization. The invention includes safe aortic diverters positionable in the ascending aorta in order to divert embolic material of all sizes away from the carotid arteries, thereby washing emboli downstream into the thoracic and peripheral vasculature. The devices of the present invention are adapted to be placed in the ascending and transverse aorta in order to divert embolic material away from the carotid arteries. This embolic matter includes but is not limited to atheromatous fragments or material, thrombus, globules of fat, air bubbles, clumps of bacteria and/or other foreign matter, tumor cells, or any other bits of tissue. The aortic diverters of the present invention can be placed surgically, endoscopically or percutaneously, and either permanently or temporarily.

In one embodiment of the invention the aortic diverter includes two components. The first component is a hollow tube, which is substantially cylindrical, conical or frustoconical in shape. The hollow tube is an appropriate size to fit within the lumen of the ascending aorta. The proximal end of the hollow tube is adapted to fill the lumen of the aorta so that substantially all blood entering the ascending aorta from the heart must travel through the hollow tube in order to continue past the ascending aorta and into the other arteries leading to the rest of the human body. The second component is an anchoring mechanism for securing the hollow tube to the lumen of the aorta.

In another embodiment the aortic diverter also includes two components. The first component is a hollow tube, which is substantially cylindrical, conical or frustoconical in shape. The hollow tube is an appropriate size to fit within the lumen of the ascending aorta. The proximal end of the hollow tube is adapted to fill the lumen of the aorta so that substantially all blood entering the ascending aorta from the heart must travel through the hollow tube in order to continue past the ascending aorta and into the other arteries leading to the rest of the human body. The second component is a sleeve secured to the proximal end of the hollow tube. The sleeve can be substantially rigid and circumferentially sized to frictionally anchor the hollow tube to the lumen of the aorta.

In another embodiment, the aortic diverter is a flat, planar, snowshoe device that can be placed across the apex of the aorta in order to prevent emboli from flowing into the carotid arteries. The snowshoe diverter comprises a planar tongue and a handle, and can also include supports or legs mounted on either or both sides of the tongue. The handle is attached to the proximal end of the tongue for convenient connection to an introducing device such as a cannula, and is also useful for easy orientation and placement of the snowshoe diverter within the aorta. The handle itself can be hollow, thus acting as a cannula to supply filtered blood to the carotid arteries as well as the descending aorta. The hollow cannulated handle can be attached to the tongue such that blood flowing out of the handle and into the aorta is partitioned by the tongue to flow either anterior or posterior the tongue. Alternatively, the cannulated handle can be attached to the tongue so that all blood flowing out of the handle and into the aorta flows anterior the tongue. Alternatively, the cannulated handle can be attached to the tongue so that all blood flowing out of the handle and into the aorta flows posterior the tongue. Alternatively, the handle can be solid with no lumen for blood flow. The handle can also be flexible and bendable in order to move the handle out of the way of the surgeon. The tongue of the snowshoe diverter has a compliant framework that allows conformance with naturally irregular interval wall structures within the aorta. The framework allows the size of the tongue to be reduced allowing for introduction through small incisions, thus minimizing aortic trauma. Thus, the tongue can be rolled or folded up in any direction or manner. The framework can comprise rings that are circular or oval. Alternatively, the framework can be a figure "8" suspension frame. The tongue also has a thin, compliant membrane that is impermeable to emboli. The membrane can be made of a mesh material that may be cotton based, Teflon, nitinol, urethane or polyurethane, any combination of the above, or a combination of the above along with wire. Alternatively, the tongue can be made of material that is impermeable to blood, but have one or more way valves allowing unidirectional blood flow. The tongue can be flexible and/or elastomeric, thus enabling the tongue to be rolled or folded up in any direction or manner. The tongue can be amoeba shaped, curved or billowed, tapered, or a combination thereof.

The methods of the present invention relate to the prevention of cerebral embolization. Cerebral embolization can occur when emboli found in the bloodstream are carried to the brain and become lodged in the smaller blood vessels of the brain, thus obstructing blood flow to an area of the brain, which can result in a stroke. One way of protecting patients against cerebral embolization is by preventing emboli from reaching the smaller blood vessels in the brain.

In one method of the invention an aortic diverter is provided. The aortic diverter is inserted into the aortic arch in the region of the carotid arteries. The surgeon secures the aortic diverter to the lumen of the aorta so that the proximal end of the aortic diverter extends upstream of the brachiocephalic trunk while the distal end of the aortic diverter extends downstream of the left subclavian artery. In the uncommon case where the carotid arteries directly connected to the aortic arch are just the left and right branch of the brachiocephalic trunk (see Anne R. Agur, Grant's Atlas of Anatomy 52 (9th ed., Williams & Wilkins 1991) (1943) (incorporated herein by reference)), the distal end of the aortic diverter extends downstream of the left brachiocephalic trunk. With the aortic diverter placed in the ascending aorta in such a manner, emboli entering the ascending aorta will necessarily have to flow through the aortic diverter and exit the distal end of the aortic diverter downstream of the carotid arteries, thus reducing the likelihood that emboli will reach the openings leading into the carotid arteries.

In another method the surgeon provides an aortic diverter comprising a planar filter material which is impermeable to emboli but not to blood. The surgeon inserts the filter material into the aortic arch in the region of the carotid arteries. The surgeon secures the filter material to the aortic lumen so that it completely covers all of the openings leading from the aorta into the carotid arteries such that blood flowing into the carotid arteries is filtered of embolic material. The embolic material is not trapped on the filter but is washed downstream of the left subclavian artery or the left brachiocephalic trunk by the stream of blood rushing through the aorta into the peripheral vasculature.

In another method the surgeon provides an aortic cannula. The surgeon then penetrates the wall of the aorta with the aortic cannula, which can have an inflatable balloon occluder concentrically disposed on its distal end. The aortic cannula is sutured to the wall of the aorta to prevent loss of blood. The balloon occluder can be inflated to prevent back-flow of blood towards the region of the heart. The surgeon then provides the snowshoe diverter previously described. The surgeon then inserts the snowshoe diverter through the aortic cannula and into the aortic arch in the region of the carotid arteries, thus preventing emboli from flowing into the carotid arteries. Alternatively, the snowshoe diverter can be integral with the aortic cannula and disposed on the distal end of the aortic cannula. The surgeon then provides a blood-return cannula. If the handle of the snowshoe diverter is hollow (i.e., cannulated), the surgeon can connect the blood-return cannula to the handle of the snowshoe diverter such that it is in fluid communication with the handle. If the handle of the snowshoe diverter is not hollow, then the surgeon can connect the blood-return cannula to the aortic cannula such that it is in fluid communication with the aortic cannula. Alternatively, the surgeon can insert the blood-return cannula through the wall of the aorta either upstream or downstream of the point of insertion of the aortic cannula. When protection from cerebral embolization is no longer necessary, the surgeon removes the snowshoe diverter from the aorta.

In another method, an aortic cannula with a snowshoe aortic diverter attached to its distal end is introduced. The aortic cannula is inserted through the wall of the aorta and the snowshoe diverter is positioned in the region of the carotid arteries. The aortic cannula can be inserted through the wall of the aorta while the snowshoe diverter fully deployed. Alternatively, the snowshoe diverter can be hidden inside the lumen of the aortic cannula until after the aortic cannula is inserted through the wall of the aorta. The snowshoe diverter can then be deployed and positioned over the carotid arteries. The snowshoe diverter extends over all of the openings leading into the carotid arteries. The aortic cannula is sutured to the wall of the aorta to prevent loss of blood. A cardioplegia cannula comprising an opening in its distal end is then introduced. The cardioplegia cannula also has an inflatable balloon occluder concentrically mounted around its distal end. The cardioplegia cannula is inserted through the wall of the aorta and sutured to the wall of the aorta to prevent loss of blood. The balloon occluder is inflated to prevent all fluid flow downstream thereof, and then cardioplegia solution is delivered to the heart through the opening in the distal end of the cardioplegia cannula. Blood from a bypass machine is introduced into the aorta through aortic cannula. Blood flowing out of the distal end of the cannula and into the aorta can be partitioned by the snowshoe diverter such that some of the blood flows to the carotid arteries superior to the snowshoe diverter while the rest of the blood flows anterior the snowshoe diverter and toward the descending aorta and peripheral vasculature. Alternatively, the snowshoe device can be attached to the distal end of the aortic cannula in such a way as to divert substantially all blood exiting the distal end of the cannula to either the carotid arteries or the peripheral vasculature.

In another method the surgeon provides an aortic diverter, which is a substantially cylindrical, conical or frustoconical hollow tube comprising a wall that is impermeable to emboli. The hollow tube is substantially flexible, is in a compressed state, and is releasably carried by an intravascular catheter for percutaneous delivery into the aorta. When deployed, the hollow tube allows blood to flow through the tube, and the proximal end of the hollow tube is circumferentially sized to completely fill the lumen of the aorta. The surgeon introduces the intravascular catheter containing the compressed aortic diverter into the vascular system. The surgeon advances the intravascular catheter into the aortic arch to the region of the carotid arteries. The surgeon deploys the aortic diverter so that the aortic diverter radially expands to contact the lumen of the aorta. In the fully deployed state, the proximal end of the aortic diverter should completely fill the lumen of the aorta and should extend upstream of the brachiocephalic trunk. The distal end of the aortic diverter should extend downstream of the left subclavian artery (or the left brachiocephalic trunk in those patients having this as the most downstream carotid artery) so that when emboli exit the distal end of the aortic diverter, they are downstream of the carotid arteries, thus reducing the likelihood that they will reach the openings leading into the carotid arteries. The surgeon then secures the aortic diverter to the lumen of the aorta, either by friction of contact or by other means discussed herein.

The present invention addresses the dangers associated with cerebral embolization. Specifically, embolization contributes significantly to problems such as stroke, lengthy hospital stays, and, in some cases, death.

Embolic material, which has been detected at 2.88 mm in diameter, will generally range from 0.02 mm (20 μm) to 5 mm, and consists predominantly of atheromatous fragments dislodged from the aortic wall and air bubbles introduced during dissection, but also includes platelet aggregates which form during cardiac surgery, thrombus in general, globules of fat, clumps of bacteria and/or other foreign matter, tumor cells, or any other bits of tissue. These emboli enter either the cerebral circulation or systemic arterial system. Those entering the cerebral circulation obstruct small arteries and lead to macroscopic or microscopic cerebral infarction, with ensuing neurocognitive dysfunction.

It is an object of the present invention to eliminate or reduce the incidence of cerebral embolization. The present invention is intended to divert emboli away from the carotid arteries, which direct blood to the brain. This diversion prevents strokes, which can lead to lengthy hospital stays, damage to the brain, and sometimes death. The present invention is particularly suited for those who are at high risk of suffering from cerebral embolization, such as elderly patients and those who have atheromatosis, as well as those patients undergoing cardiac surgery, which has been shown to result in the release of emboli into the bloodstream. See, for example, Barbut et al., "Cerebral Emboli Detected During Bypass Surgery Are Associated With Clamp Removal," Stroke, 25(12):2398–2402 (1994).

As for the devices, one object is to provide safe and reliable devices that are easy to manufacture and use. A further object is to provide devices that may be used in the aorta, and especially in the ascending aorta. Yet another object is to provide devices that will reduce the likelihood of cerebral embolization, especially in those patients who are at high risk for cerebral embolization. Yet another object is to provide devices that can be introduced into the aorta and secured to the lumen of the aorta with minimal trauma to the patient.

The devices disclosed herein have the following characteristics: they can withstand high arterial blood flow rates for an extended time; they can expand and contract with the wall of the aorta; they can be made of a monolithic molded material that is impermeable to blood as well as emboli, such as Teflon impregnated with an anti-thrombogenic coating or nitinol impregnated with an anti-thrombogenic coating, or they can be made of material that is impermeable to emboli and not blood, such as a mesh, a woven material, or a thin polymer; they can be biodegradable; they can include openings on their walls of any shape or predetermined pattern, wherein the openings are covered in material that is impermeable to emboli; they can be introduced surgically, endoscopically, or percutaneously with cannulas or intravascular catheters introduced through the femoral artery, subclavian artery, brachiocephalic artery, or a cut-down to the abdominal aorta; they can be left in the aorta permanently or temporarily; they can be secured to the lumen of the aorta through various mechanisms including sutures, surgical clips, hooks, adhesive material, substantially rigid sleeves, or frictional engagement; they can be flat, conical, frustoconical, or cylindrical; they can be radially self-expanding or expanded mechanically; they can be substantially rigid or substantially flexible like a "windsock;" and they can be sized to fit vessels of varying sizes.

As for the methods of this invention, an object is to prevent cerebral embolization. The methods of this invention can be employed on various patients, especially those at high risk for cerebral embolization, in order to reduce the incidence of cerebral embolization, which can lead to neurologic or cognitive complications and death. Another object is to temporarily or permanently divert emboli away from the carotid arteries by forcing emboli downstream of the openings leading from the aorta into the carotid arteries. Another object is to provide a method for eliminating or minimizing cerebral embolization during invasive cardiac procedures. Yet another object is to provide a method of introducing an aortic diverter intravascularly or with a cannula for minimal trauma to the patient.

BRIEF DESCRIPTION OF THE DRAWINGS

Reference is next made to a brief description of the drawings, which are intended to illustrate aortic diverters and methods of their use. The drawings and detailed description which follow are intended to be merely illustrative and are not intended to limit the scope of the invention as set forth in the appended claims.

FIG. 15 is a three-dimensional view of a tongue of a snowshoe aortic diverter, wherein the tongue is flat and has supports.

FIG. 15A is a three-dimensional view of a tongue of a snowshoe aortic diverter, wherein the tongue is curved or billowed.

FIG. 15B is a three-dimensional view of a tongue of a snowshoe aortic diverter, wherein the tongue is tapered in that the proximal end of the tongue is wider than the distal end thereof.

FIG. 15C is a three-dimensional view of a tongue of a snowshoe aortic diverter, wherein the tongue is tapered in that the proximal end of the tongue is narrower than the distal end thereof.

FIG. 16 is a longitudinal view of a snowshoe aortic diverter positioned to prevent emboli from entering the carotid arteries, wherein a blood-return cannula is inserted through the wall of the aorta in order to allow blood into the aorta.

FIG. 24 is a top view of a flat snowshoe aortic diverter with a one-way valve.

FIG. 24A is a cross-sectional view through section A—A of the snowshoe aortic diverter depicted in FIG. 24.

FIG. 24B depicts the flap valve of a diverter as shown in FIG. 24.

FIG. 25 is a top view of a flat snowshoe aortic diverter with a one-way valve and a ring suspension frame.

FIG. 25A is a cross-sectional view through section A—A of the snowshoe aortic diverter depicted in FIG. 25.

FIG. 26 is a top view of a flat snowshoe aortic diverter with a FIG. 8 suspension frame.

DETAILED DESCRIPTION

Figure 1:
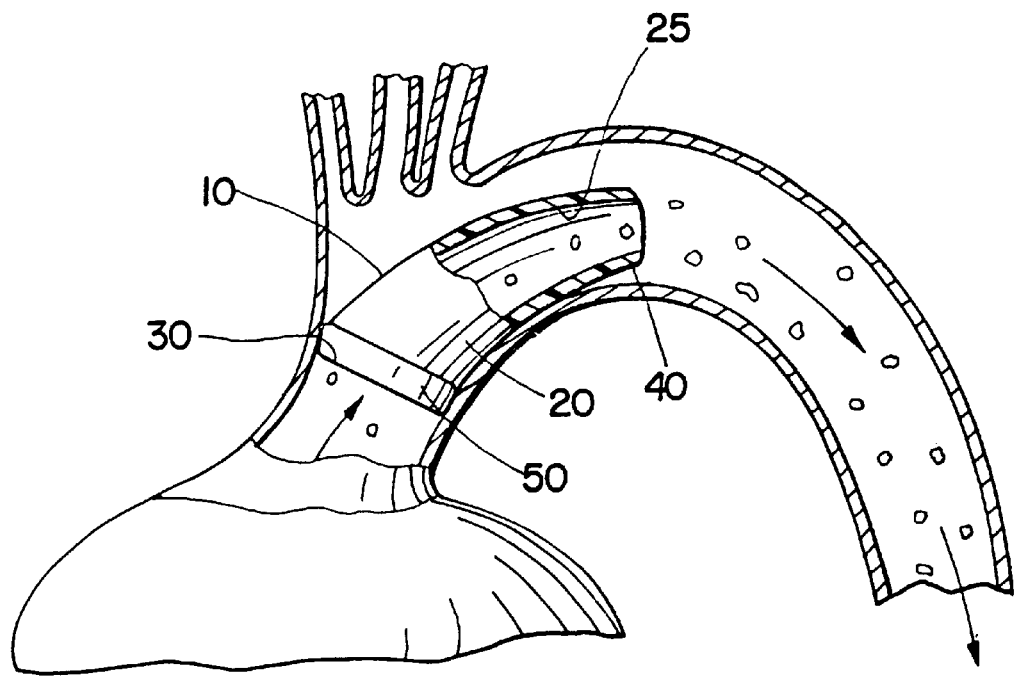
FIG. 1 is a longitudinal view of an aorta diverter according to one embodiment, showing the aortic diverter positioned within the ascending aorta.

Referring more particularly to the drawings, FIG. 1 shows one embodiment of the aortic diverter 10 for use herein. The aortic diverter 10 is a hollow tube 20 with an anchoring mechanism 50 in connection with the proximal end 30 of the hollow tube 20. The hollow tube 20 comprises a substantially cylindrical or conical wall 25, which is impermeable to blood. The wall 25 of the hollow tube 20 can be made of a monolithic molded material. This material can be urethane, Teflon or nitinol, any of which may be impregnated with an anti-thrombogenic coating. However, other materials that are impermeable to blood can also be used, including materials that are biodegradable. The hollow tube 20 has a proximal end 30 terminating in a substantially circular edge adapted to fill the lumen of the aorta or the anchoring mechanism 50. The hollow tube also has a distal end 40.

Both the proximal end 30 and distal end 40 of the hollow tube 20 are substantially open. When the aortic diverter 10 is placed in the aorta, blood flows from the heart, into the aorta, and must enter the proximal end 30 of the hollow tube 20, flow through the hollow tube 20, and exit through the distal end 40 of the hollow tube 20.

Secured to the proximal end 30 of the hollow tube 20 is an anchoring mechanism 50 for securing the aortic diverter 10 to the lumen of the aorta. The anchoring mechanism 50 can be a sleeve adapted to frictionally engage the lumen of the aorta or any one of the following: one or more sutures, one or more clips, one or more hooks, or adhesive material. Alternatively, the anchoring mechanism 50 may simply comprise the proximal end 30 of the hollow tube 20 itself, which may be adapted to frictionally engage the lumen of the aorta. For example, the proximal end 30 of the hollow tube 20 may be substantially rigid, thus making it capable of being lodged into the lumen of the aorta.

The hollow tube 20 can be substantially rigid or a flexible windsock. Furthermore, where the hollow tube 20 is a flexible windsock, the proximal end 30 may still be substantially rigid for frictional engagement with the lumen of the aorta.

The aortic diverter 10 depicted in FIG. 1 prevents emboli from reaching the carotid arteries because it prevents lateral blood flow to the carotid arteries. Blood reaches the carotid arteries due to back-flow over the distal end 40 of the aortic diverter 10. Atherembolic material continue downstream because they are less susceptible to being swept retrograde due to their greater density over blood.

Figure 2:
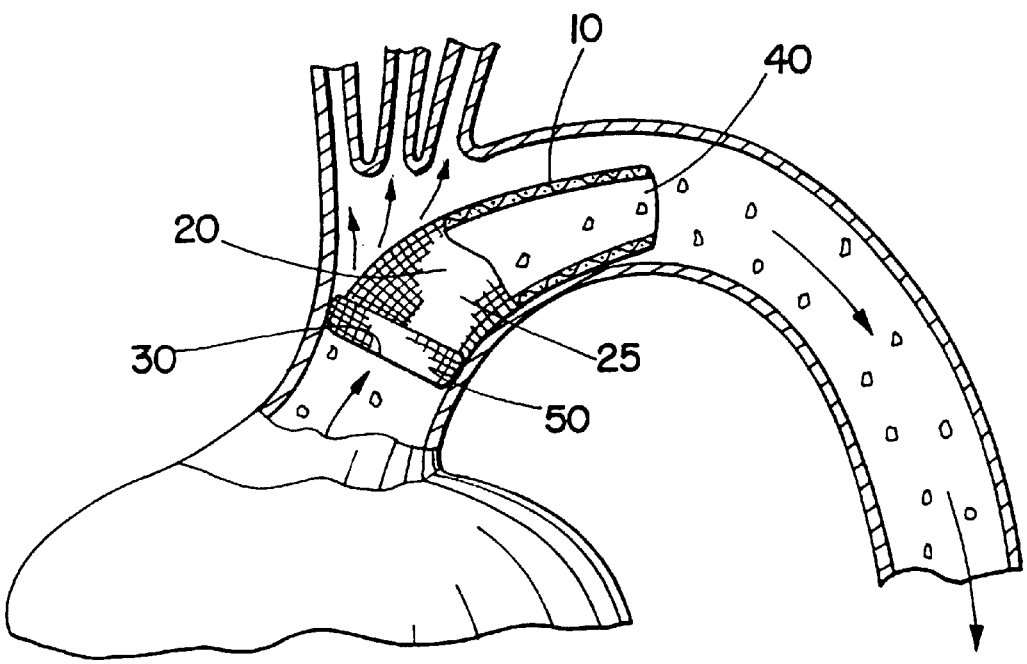
FIG. 2 is a longitudinal view of an aortic diverter according to another embodiment, and in which the aortic diverter is positioned within the ascending aorta and is made of a material that is permeable to blood but impermeable to emboli.
Figure 3:
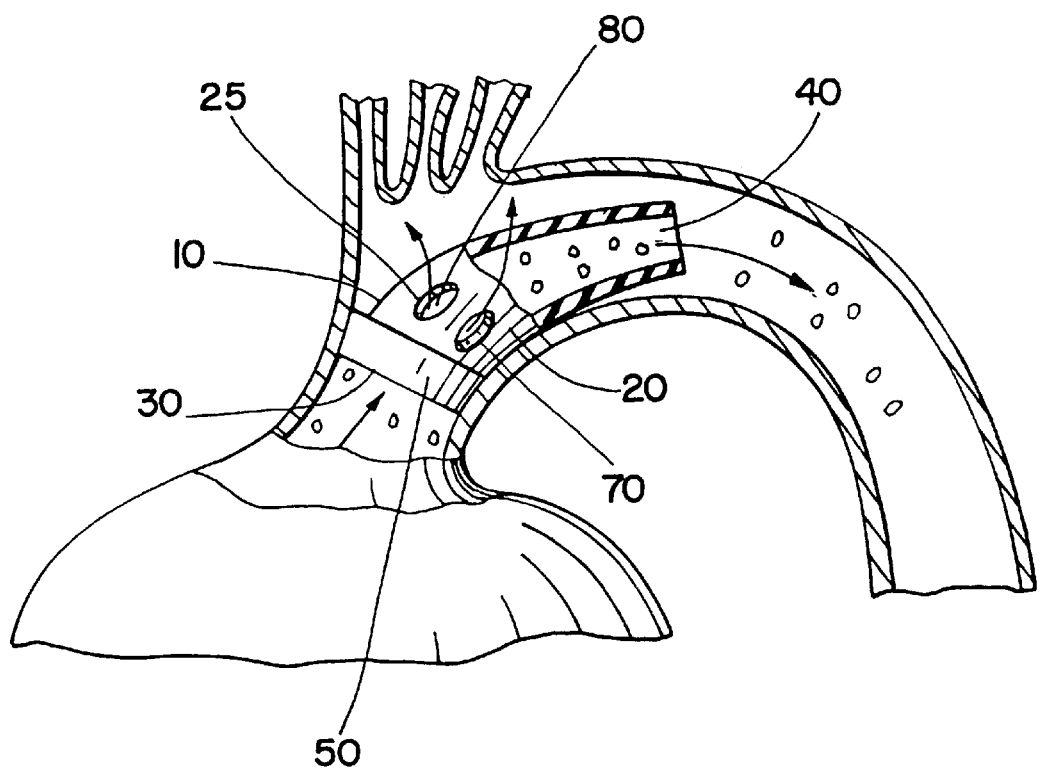
FIG. 3 is a longitudinal view of an aortic diverter according to another embodiment, and in which the aortic diverter is positioned within the ascending aorta and is made of a material that is impermeable to blood, wherein the aortic diverter has openings on its surface, and wherein the openings are covered with material that is permeable to blood but impermeable to emboli.

Referring now to both FIGS. 2 and 3, FIG. 2 shows the aortic diverter 10 with a wall 25 that is made of a material that is permeable to blood but impermeable to emboli. The wall 25 can be made of a mesh material, a woven material, a thin polymer, or any material that is permeable to blood but impermeable to emboli, including material that is biodegradable. Furthermore, as depicted in the aortic diverter 10 of FIG. 3, the wall 25 of the hollow tube 20 can be impermeable to blood, but have openings 70 that are covered with material 80 that is permeable to blood yet impermeable to emboli. When placed in the aorta, blood flows from the heart, into the aorta, and must enter the proximal end 30 of the hollow tube 20, flow through the hollow tube 20, and exit either through the distal end 40 of the hollow tube 20 or laterally through the blood-permeable wall 25 of FIG. 2 or the openings 70 of FIG. 3. Since the wall 25 of FIG. 2 and the openings 70 of FIG. 3 are impermeable to emboli, emboli are washed downstream with the current of blood that takes the emboli to the peripheral vasculature. The distal end of the aortic diverter 10 may also be adapted to completely fill the lumen of the aorta such that there is no backflow of blood to the carotid arteries. There is no need for backflow because blood flows to the carotid arteries laterally through the wall 25 of FIG. 2 or the openings 70 of FIG. 3.

The aortic diverter 10, depicted in FIGS. 2 and 3 respectively, prevent emboli from reaching the carotid arteries because emboli cannot laterally pass through the wall 25 of FIG. 2, or alternatively the openings 70 of FIG. 3. Furthermore, the danger of backflow carrying emboli to the carotid arteries is reduced because the pressure caused by lateral blood flow through the wall 25 of FIG. 2, or alternatively the openings 70 of FIG. 3, counteracts with the backflow pressure, reducing the amount of blood that reaches the carotid arteries due to backflow. Moreover, when the distal end 40 of the aortic diverter 10 is adapted to fill the lumen of the aorta, there is no backflow to the carotid arteries. In either case, emboli are washed downstream and into the peripheral vasculature without ever reaching the carotid arteries.

Referring now only to FIG. 3, the openings 70 can be of any shape including circles, ovals, rectangles, octagons, squares, or slits. The wall 25 of the hollow tube 20 may include one opening 70 or a plurality of openings 70. The openings 70 can be radially disposed along the circumference of the hollow tube 20 or longitudinally disposed along the length of the hollow tube 20. The openings can be one or more continuous rings disposed along the circumference of the hollow tube 20, or one or more continuous columns longitudinally disposed along the length of the hollow tube 20.

Referring now to FIGS. 1, 2 and 3, the substantially rigid proximal end 30 may be lodged into the lumen of the aorta by surgically placing the proximal end 30 at a point where the proximal end 30 has a larger circumference than the lumen of the aorta. Alternatively, the hollow tube 20 can be introduced into the aorta in a compressed, but rigidly expandable state, either percutaneously or surgically. The hollow tube 20 can then be allowed to self-expand or forced to radially expand into frictional engagement with the lumen of the aorta.

Figure 7:
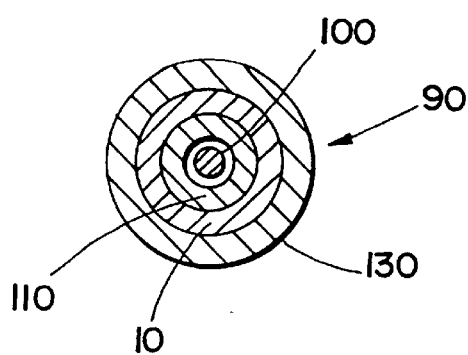
FIG. 7 is a cross-sectional view through section line 7—7 of the device depicted in FIG. 6.
Figure 6:
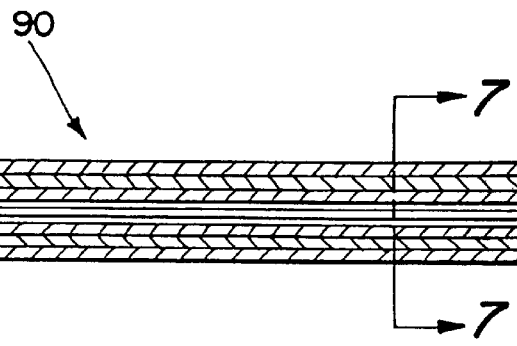
FIG. 6 is a longitudinal view of an intravascular catheter with associated self-expanding aortic diverter and removable actuation sleeve.

FIGS. 6 through 10 show one method of introducing and positioning aortic diverter 10 in the ascending aorta. FIGS. 6 through 10 show aortic diverter 10, which is self-expanding, loaded onto assembly 90 for percutaneous delivery. The intravascular catheter 110 operates over a standard guidewire 100. Aortic diverter 10 expands between a compressed state and a radially expanded state. FIGS. 6 and 7 show aortic diverter 10 contained in a compressed state by generally inelastic sleeve 130, which surrounds diverter 10 and prevents it from self-expanding.

Figure 8:
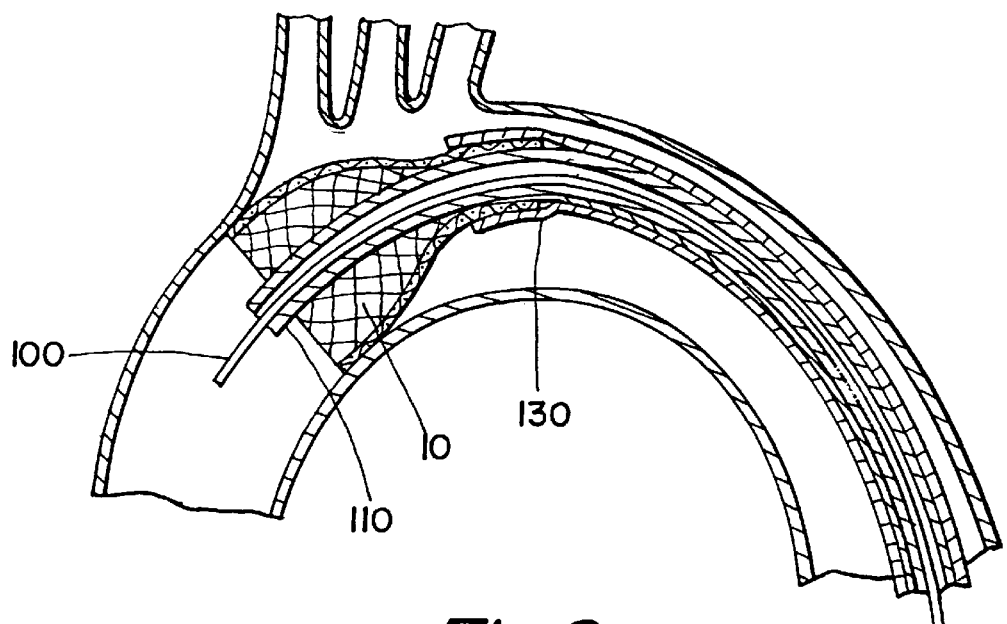
FIG. 8 is a longitudinal view of the device depicted in FIG. 7 positioned within the ascending aorta, wherein the actuation sleeve is shown being removed to release the self-expanding aortic diverter, and the aortic diverter is shown in a self-expanding state.
Figure 9:
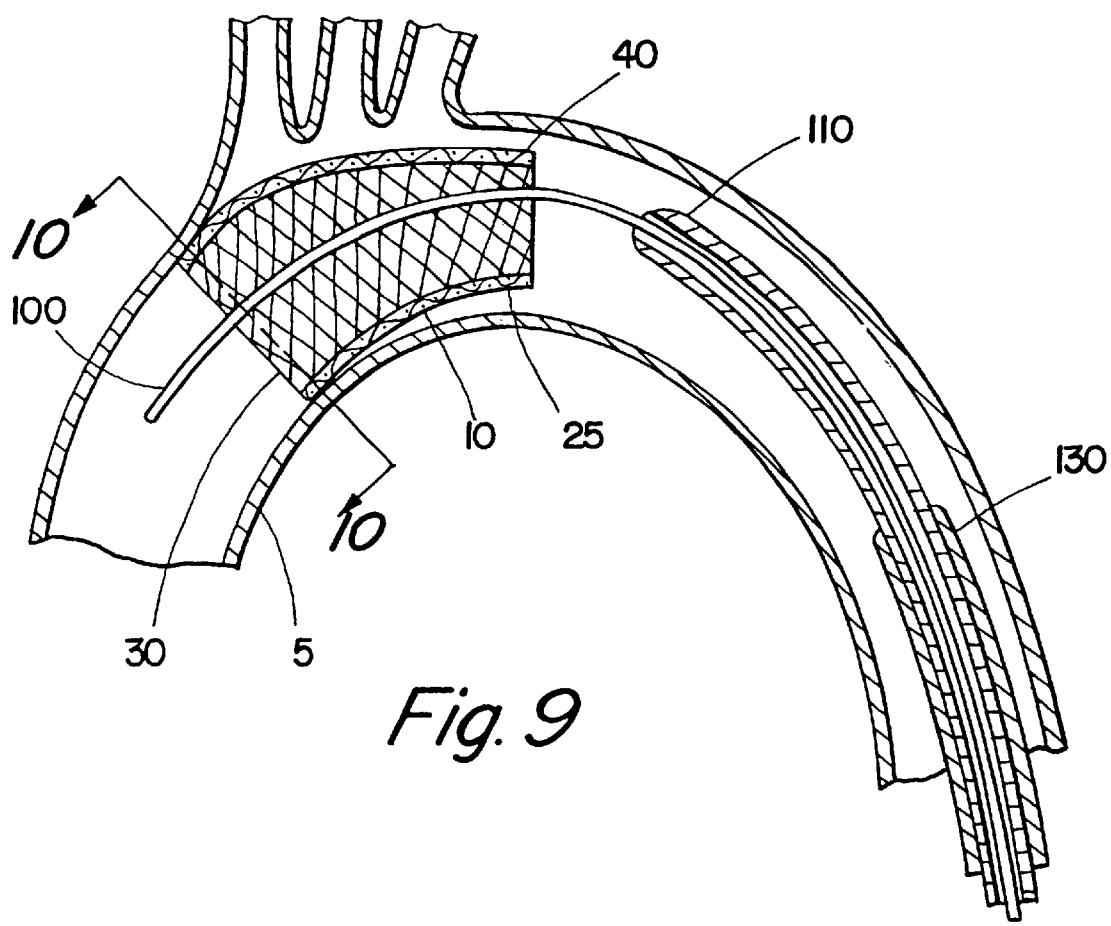
FIG. 9 is a longitudinal view of the device depicted in FIG. 8 positioned within the ascending aorta, wherein the catheter is being removed and the aortic diverter is in a fully expanded and operable state within the ascending aorta.
Figure 10:
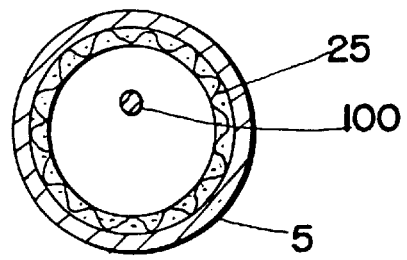
FIG. 10 is a cross-sectional view through section line 10—10 of the aortic diverter as it is percutaneously delivered to the ascending aorta.
Figure 11:
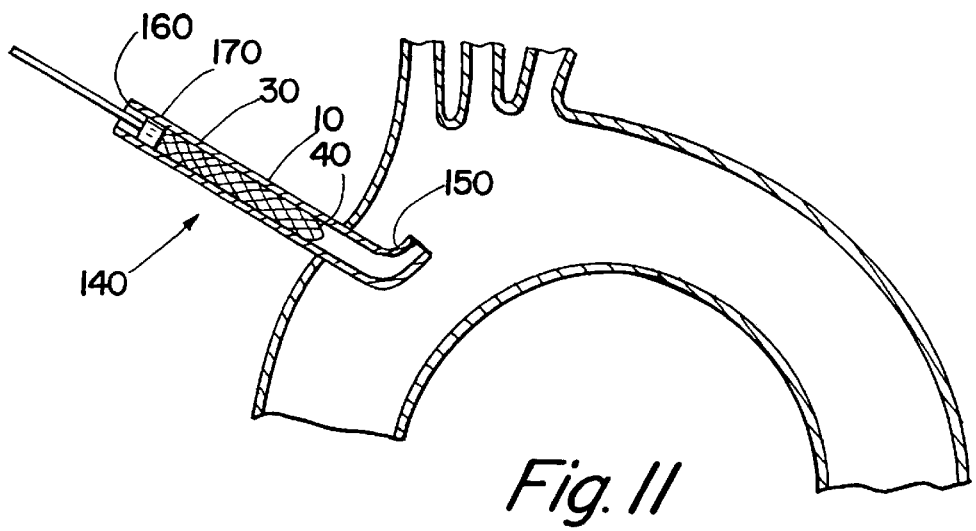
FIG. 11 is a longitudinal view of a cannula penetrating the lumen of the ascending aorta, wherein an aortic diverter is disposed within the cannula.
Figure 12:
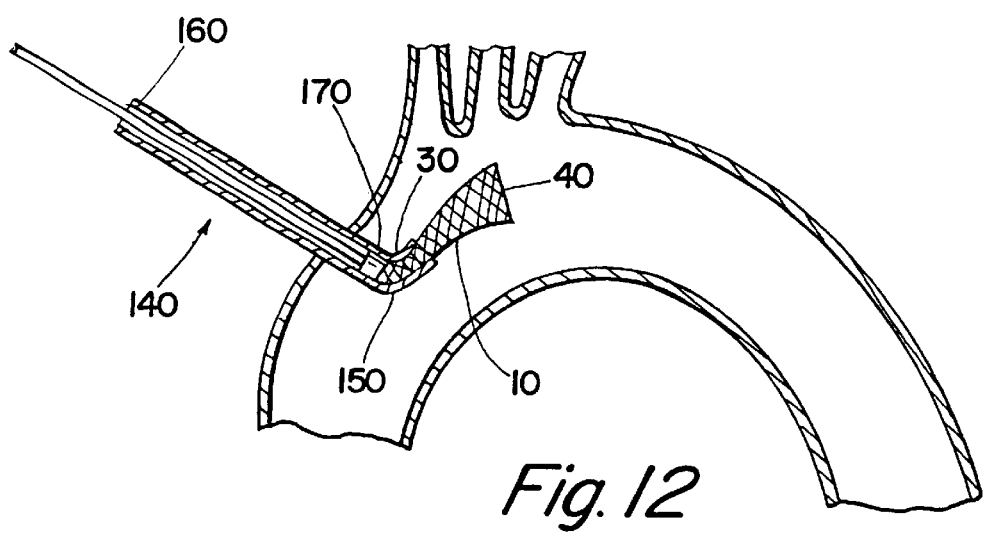
FIG. 12 is a longitudinal view of the device depicted in FIG. 11, wherein the self-expanding aortic diverter is pushed through the cannula and is expanding as it exits the cannula.
Figure 13:
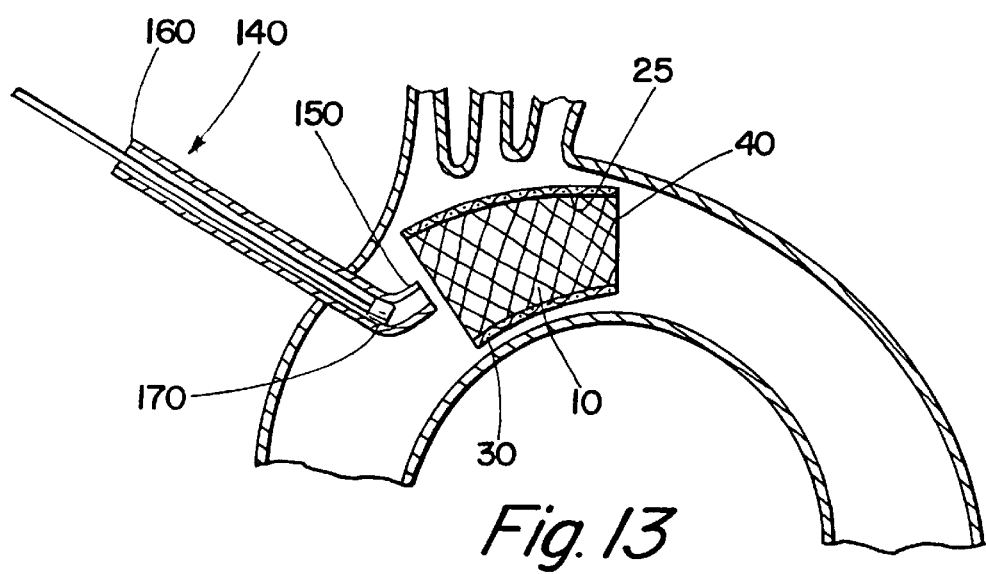
FIG. 13 is a longitudinal view of the device depicted in FIG. 11, wherein the aortic diverter is in a fully expanded and operable state within the ascending aorta.

FIG. 8 shows the intravascular catheter assembly 90 positioned in the ascending aorta. Once assembly 90 is correctly positioned, the sleeve 130 is pulled back, thus allowing aortic diverter 10 to deploy. Then, as depicted in FIG. 9, once the sleeve is completely removed, diverter 10 is released, and intravascular catheter 110 is pulled back along the guidewire and removed. The proximal end 30 of the aortic diverter 10 completely fills the lumen of the aorta so that substantially all blood flowing into the ascending aorta must pass through the aortic diverter 10. FIG. 10 is a cross sectional view through line 10—10 of FIG. 9 and shows that the wall 25 of the aortic diverter 10 is in continuous radial contact with and completely fills the lumen of the aorta 5. The distal end 40 of the aortic diverter 10 may also completely fill the lumen of the aorta 5 if the wall 25 of the aortic diverter is made of material that is permeable to blood, as in FIGS. 2 and 3. FIGS. 11 through 13 show another method of delivering the aortic diverter 10 to the ascending aorta. In this method, the aortic diverter 10 is again self-expanding, but is delivered with a cannula 140 that directly penetrates the lumen of the aorta. FIG. 11 shows the cannula 140, after having penetrated the aorta, with the aortic diverter 10 contained within the barrel of the cannula 140. Once the cannula 140 is in position for delivery of the aortic diverter 10, a piston rod 160 with a piston 170 attached to its distal end is advanced toward the distal end 150 or outlet of the cannula. As the piston rod 160 is advanced the piston 170 pushes against the proximal end 30 of the aortic diverter 10, which is in a compressed state, forcing the aortic diverter 10 toward the outlet 150 of the cannula 140. FIG. 12 shows the aortic diverter 10 emerging from the outlet 150 of the cannula 140 and self-expanding since it is no longer contained in a compressed state. FIG. 13 shows the aortic diverter 10 completely deployed and operable. The proximal end 30 of the aortic diverter 10 completely fills the lumen of the aorta such that substantially all blood flowing into the aorta from the heart must flow through the aortic diverter 10. The distal end 40 of the aortic diverter 10 may also completely fill the lumen of the aorta if the wall 25 of the aortic diverter 10 is permeable to blood but impermeable to emboli as in FIGS. 2 and 3.

Figure 4:
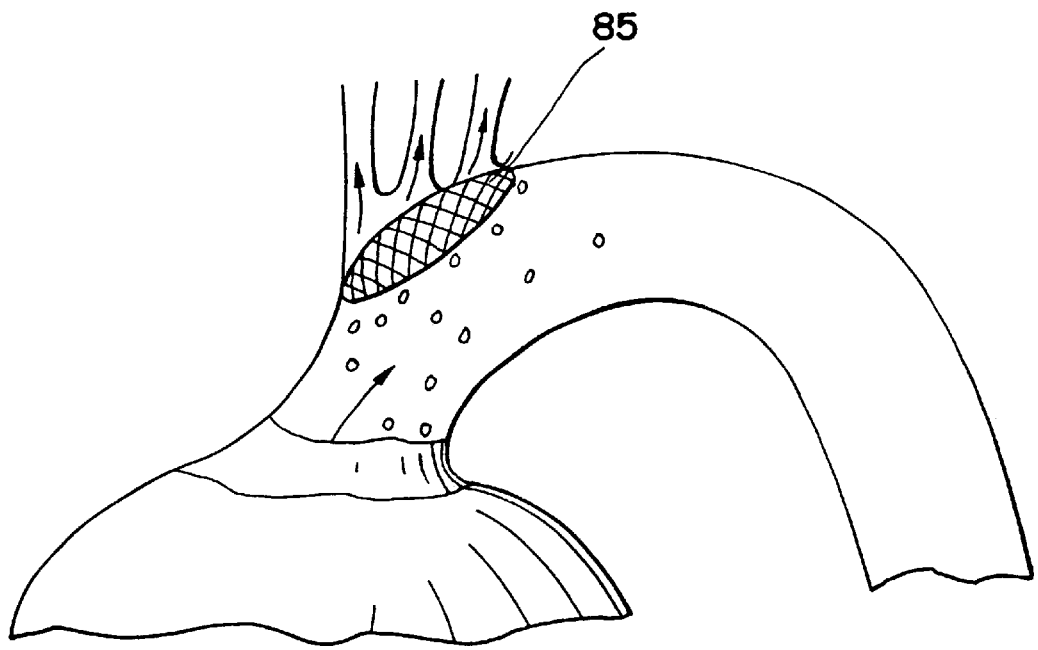
FIG. 4 is a three-dimensional drawing of an aortic diverter according to another embodiment, showing the aortic diverter positioned across the openings leading into the carotid arteries, and in which the aortic diverter is permeable to blood but impermeable to emboli.

FIG. 4 shows another embodiment of an aortic diverter 85 comprising a substantially planar filter material which is permeable to blood but impermeable to emboli. The aortic diverter 85 can be anchored to the lumen of the aorta with one of the following: one or more sutures, clips, hooks, or adhesive material. By placing the aortic diverter 85 so that it simultaneously covers all of the openings leading from the aorta into the carotid arteries, the aortic diverter 85 prevents emboli from entering the carotid arteries. As blood flows through the blood-permeable material of the aortic diverter 85, emboli are blocked and are swept downstream with the current of blood.

The aortic diverter 85 can be substantially rigid or flexible and surgically, endoscopically, or percutaneously delivered to the aorta. Percutaneous delivery can be accomplished using an intravascular catheter assembly 90 as in FIG. 6 and constructing the aortic diverter 85 so that it is self-expanding and concentrically mountable around the intravascular catheter 110. Once deployed, the aortic diverter 85 can be secured to the lumen of the aorta with various anchoring mechanisms disclosed in the preceding paragraph.

Surgical delivery of the aortic diverter 85 can be accomplished using a method similar to the one depicted in FIGS. 11–13. The aortic diverter 85 can be compressibly disposed within the barrel of the cannula 140 and constructed to self-expand when no longer constrained by the walls of the cannula 140. Again, the aortic diverter 85 can be secured to the lumen of the aorta with the various anchoring mechanisms previously disclosed.

Procedures such as incising, clamping, clamp release, and balloon occluding, which are applied during cardiopulmonary bypass, are known to cause embolization. For example, during cardiac surgery, the aorta is clamped or balloon-occluded. Because clamping and/or balloon occluding the aorta dislodges atheromatous material from the walls of the aorta, which is released into the bloodstream, an aortic diverter is needed before clamping and/or balloon occluding begins in order to divert embolic material away from the carotid arteries. Atheromatous material also accumulates behind clamps during surgery and, because removal of the clamps releases this material into the bloodstream, an aortic diverter must be maintained within the bloodstream for about four to ten minutes after removal of the clamps.

Figure 5:
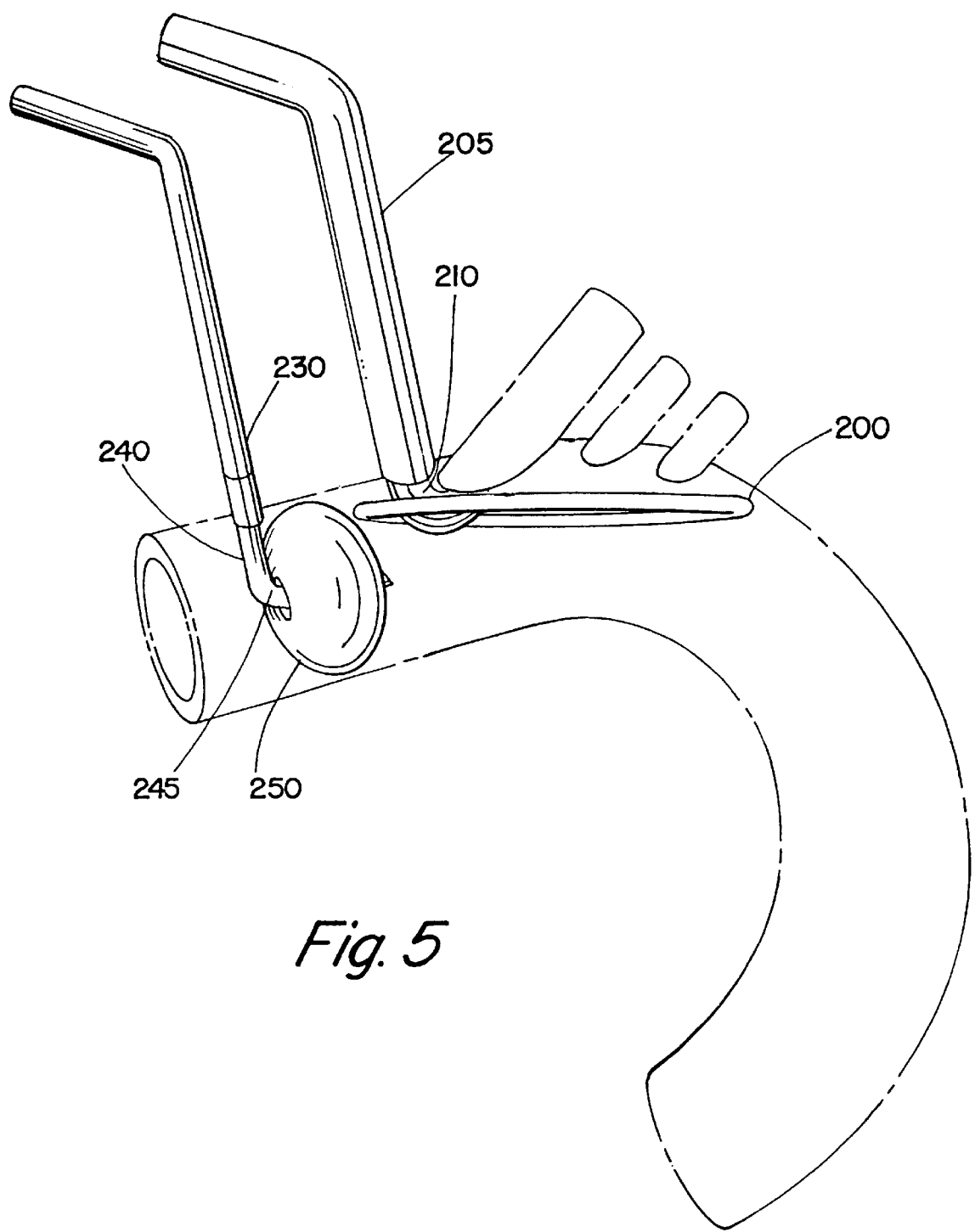
FIG. 5 is a longitudinal view of a temporary aortic diverter, wherein a cannula penetrating the lumen of the ascending aorta is used to hold the aortic diverter in position during surgery, and wherein a cardioplegia cannula with a balloon occluder is used to deliver cardioplegia solution to the heart.

FIG. 5 shows a "snowshoe" aortic diverter 200 attached to the distal end of a cannula for temporary diversion of embolic material away from the carotid arteries during cardiopulmonary bypass. For illustration purposes, the method for diverting emboli away from the carotid arteries will be described in connection with the "snowshoe" aortic diverter 200 depicted in FIG. 5. After a patient has been anaesthetized and the patient's chest has been opened in preparation for surgery, the cannula 205 with aortic diverter 200 attached to the distal end 210 of the cannula 205 is introduced into an incision made in the aorta. Alternatively, the aortic diverter 200 may be inside the cannula and advanced through the distal end 210 of the cannula 205 after the cannula 205 is introduced into the incision made in the aorta. The aortic diverter 200 is positioned in the aorta, extending over all of the openings leading to the carotid arteries, in order to ensure that emboli do not reach the brain. The cannula 205 is sutured to the aortic wall. Then a cardioplegia cannula 230 with a balloon occluder 250 attached to its distal end 245 is introduced into another incision made in the aorta. The cardioplegia cannula 230 is sutured to the aortic wall. The balloon occluder 250 is inflated in order to block all fluid flow downstream thereof, and the cardioplegia cannula 230 then delivers cardioplegic solution through an opening 240 in its distal end into the heart, thereby causing the heart to be paralyzed. Balloon occluding may inadvertently dislodge atheromatous material from the walls of the aorta and release it into the bloodstream. However, the aortic diverter 200 prevents the atheromatous material from entering the carotid arteries. Blood from a bypass machine is introduced into the aorta through the cannula 205. Once surgery is complete, bypass is discontinued, and the balloon occluder is deflated, thereby releasing more atheromatous material. The aortic diverter 200 is left in position for four to ten minutes and then removed.

Figure 14:
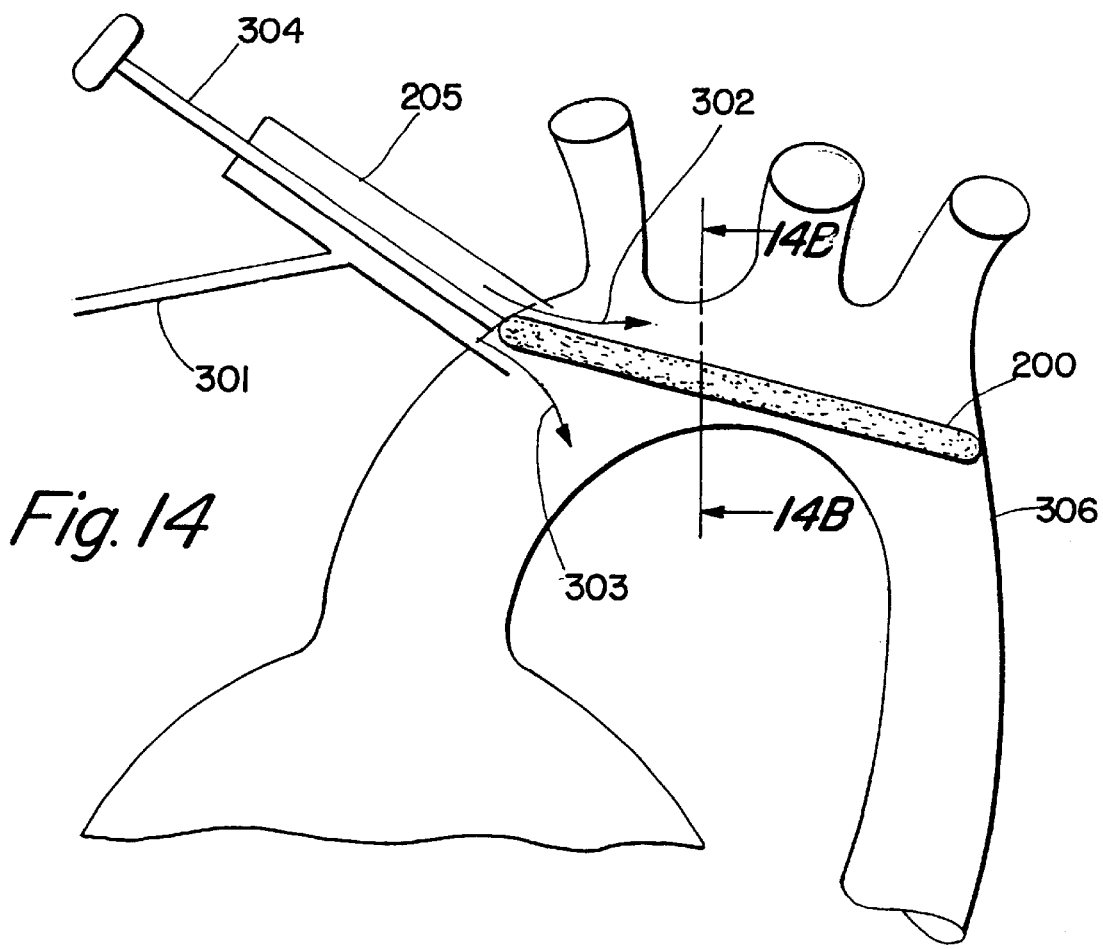
FIG. 14 is a longitudinal view of a snowshoe aortic diverter as it is inserted through the aortic cannula and into position in the aorta, wherein the blood-return cannula is in fluid communication with the aortic cannula.
Figure 14A:
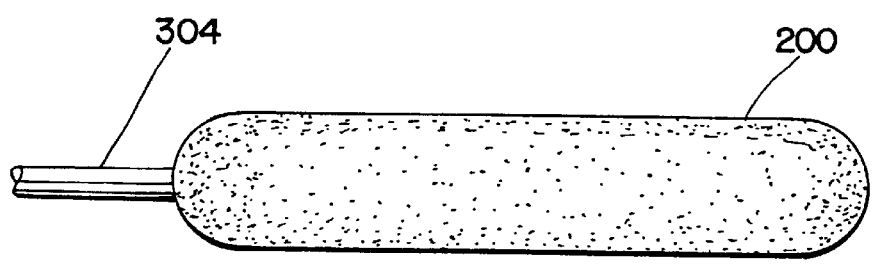
FIG. 14A is a detail of the tongue of the snowshoe diverter of FIG. 14.
Figure 14B:
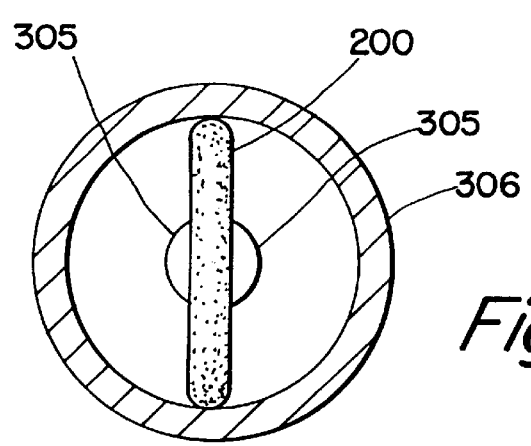
FIG. 14B is a cross-sectional view through section B—B of the snowshoe aortic diverter depicted in FIG. 14.

FIG. 14 depicts another implementation of snowshoe diverter 200 deployed within aorta 306. Cannula 205 includes side channel 301 for receiving filtered blood from a bypass machine (not shown). The blood travels through cannula 205, and is split into a first stream 302 (blood supply for carotid arteries) and a second stream 303 (blood supply for descending aorta) as it passes from blood supply channel 305 (FIG. 14B). Cannula 205 therefore delivers oxygenated blood to the aorta above and below diverter 200, so that the stream of blood is split. FIG. 14A is an expanded longitudinal view of diverter 200 with handle 304, while FIG. 14B shows a cross-section taken through section lines 14B in FIG. 14, and showing diverter 200 and blood supply channels 305.

FIGS. 15–15C show various configurations for the diverting member 200. FIG. 15 shows amoeba-shaped tongue diverter 200 having external wire supports 308 attached. FIG. 15A shows curved tongue diverter 200, which may, in some embodiments include wire supports (not shown). A diverter in the shape of a tapered tongue is depicted in FIGS. 15B and 15C. The diverter tongue may be comprised of a mesh (free of polyurethane), a mesh-polyurethane composite, or a mesh-polyurethane-wire composite. The diverter tongue may be constructed with or without wire supports.

Figure 17:
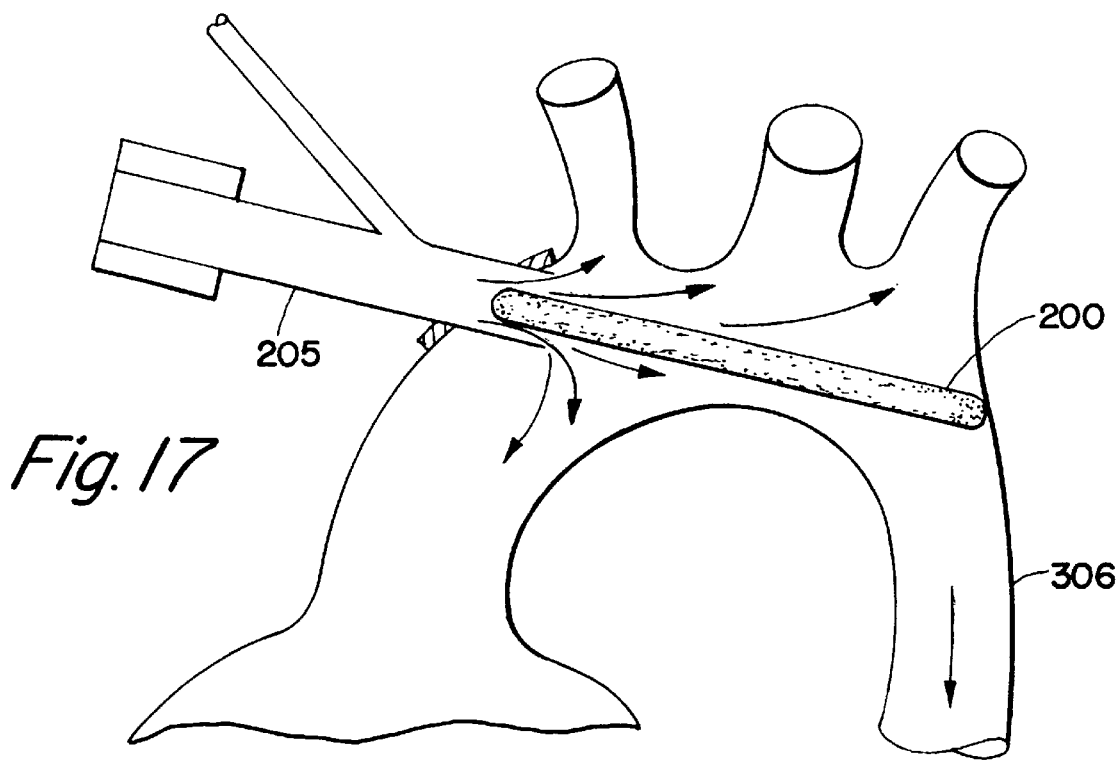
FIG. 17 is a longitudinal view of a snowshoe aortic diverter, wherein the snowshoe aortic diverter is directly connected to the distal end of an aortic cannula, wherein a blood-return cannula is in fluid communication with the aortic cannula, and wherein blood entering the aorta is directed either towards the carotid arteries or posterior to the snowshoe diverter.
Figure 18:
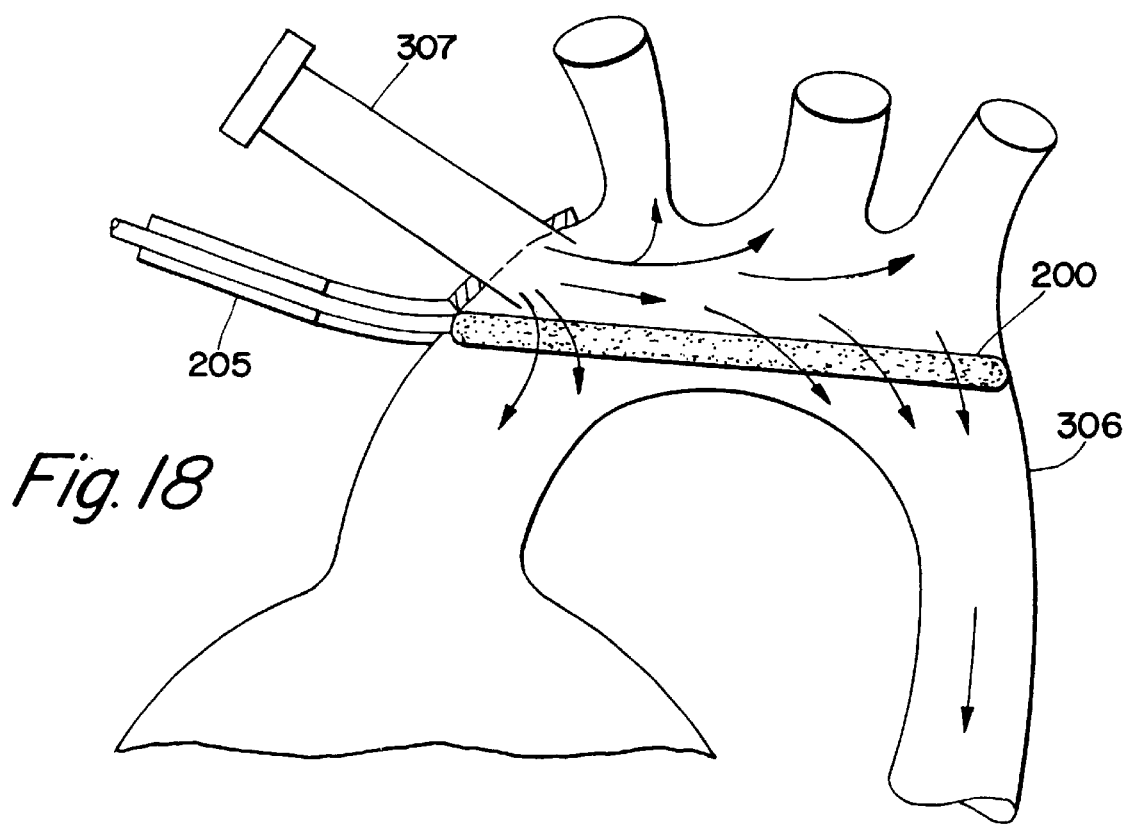
FIG. 18 is a longitudinal view of a snowshoe diverter inserted upstream from a blood-return cannula and wherein blood returning to the peripheral vasculature must first pass through the snowshoe diverter.
Figure 19:
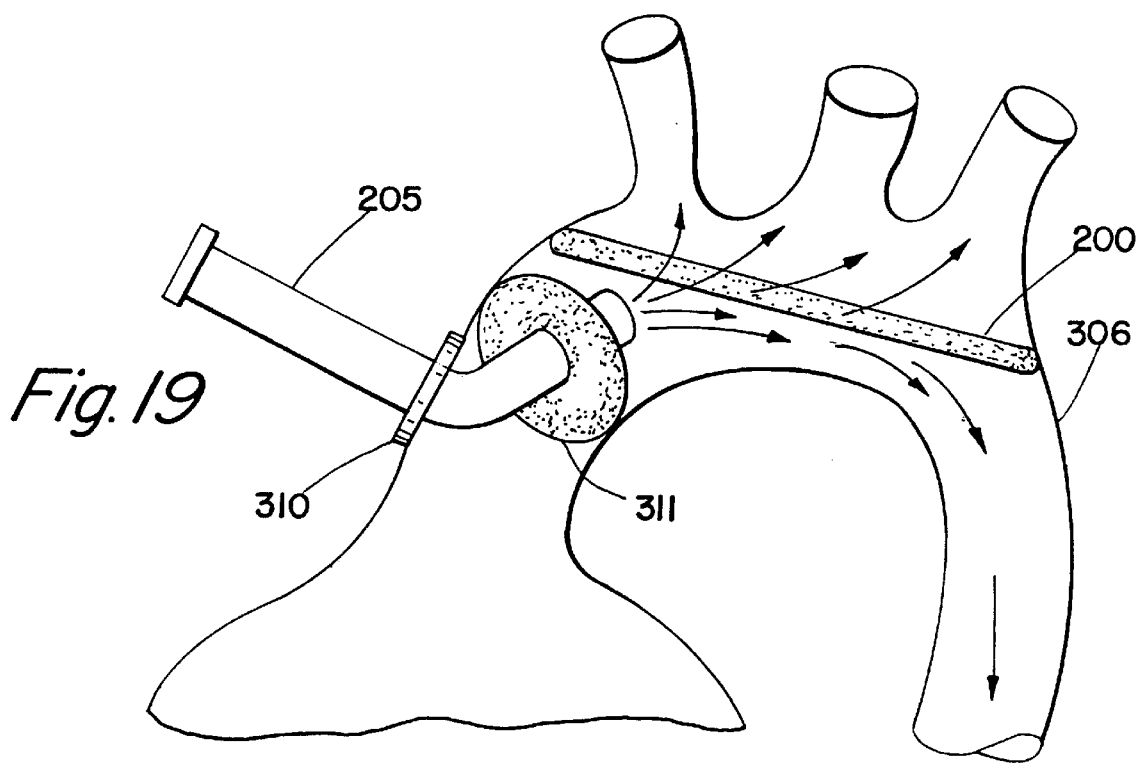
FIG. 19 is a longitudinal view of a snowshoe aortic diverter after it has been positioned in the region of the carotid arteries above an aortic cannula with a inflatable balloon occluder, wherein the aortic cannula allows blood to flow into the aorta, and wherein the snowshoe diverter prevents emboli from entering the carotid arteries.
Figure 20:
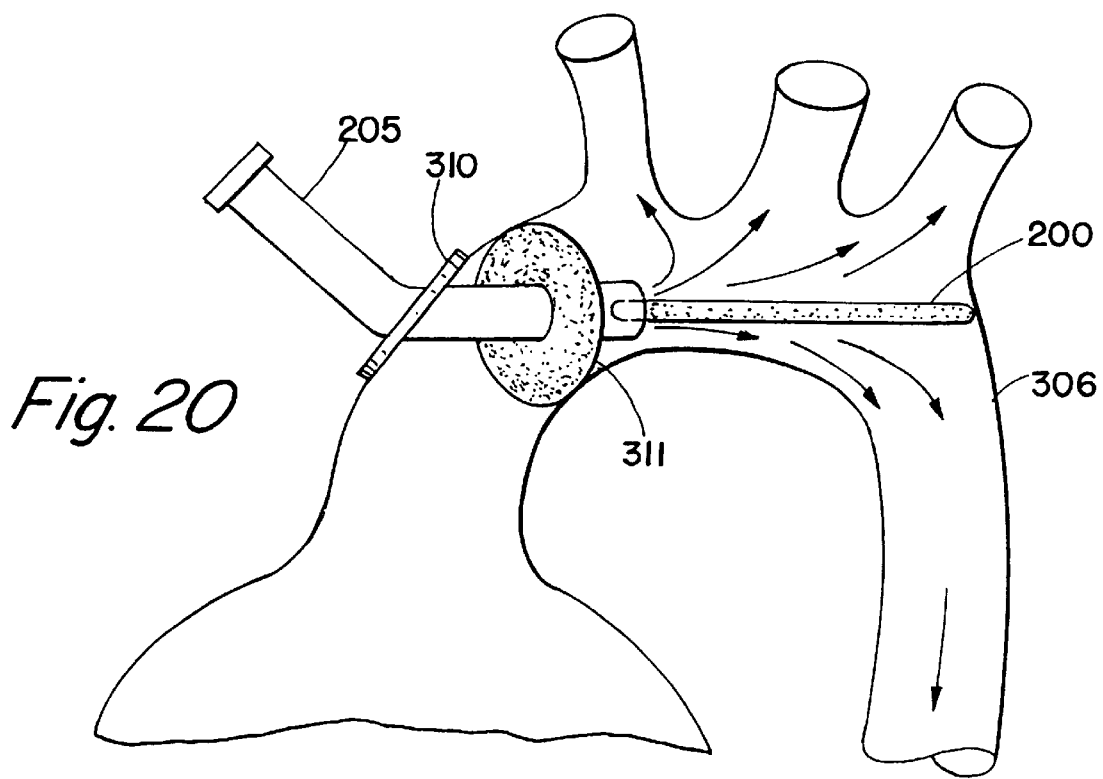
FIG. 20 is a longitudinal view of a snowshoe aortic diverter attached to the distal end of an aortic cannula with an inflatable balloon occluder, wherein blood flowing out of the distal end of the aortic cannula is diverted to flow either into the carotid arteries or anterior the snowshoe diverter and into the peripheral vasculature.

In FIG. 16, cannula 205 is used to deploy diverter 200 in aorta 306, while separate cannula 307 delivers oxygenated blood to the aorta. Diverter 200 is porous for this implementation, thus permitting blood to enter cerebral circulation by passing through diverter 200. Thus, it will be understood that the diverter tongue may be deployed above the aortic cannula (FIG. 16), below the aortic cannula (FIG. 18), or midway with respect to the aortic cannula (FIG. 17). The diverter may be integral with the cannula, separately insertable through the cannula, or inserted through a separate stick in the aorta. The diverter may be part of an aortic occluder in certain embodiments (FIGS. 19 and 20). Balloon occluder 311 is circumferentially disposed about cannula 205, and diverter 200 is deployed therethrough (FIG. 20). A top-mounted diverter structure is shown in FIG. 19, but it will be understood that a bottom-mounted structure would also be advantageous, and would deliver blood above the diverter. Cannula 205 optionally includes flange 310 to ensure proper placement and positioning through aorta 306.

Figures 21, 21A:
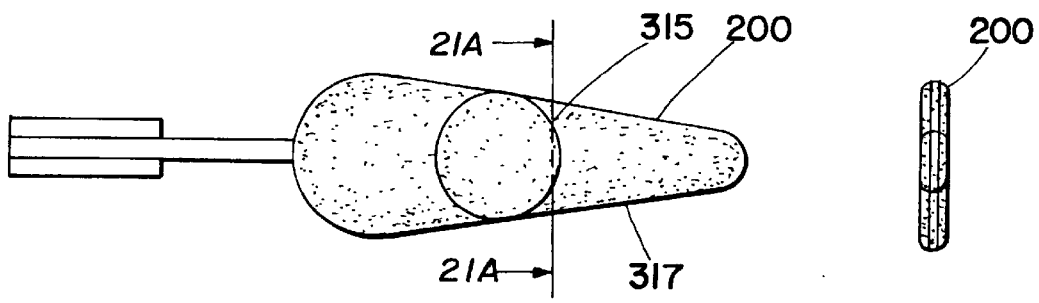
FIG. 21 is a top view of a tapered snowshoe aortic diverter with a ring suspension frame.
FIG. 21A is a cross-sectional view through section A—A of the snowshoe aortic diverter depicted in FIG. 21.
Figures 22, 22A:
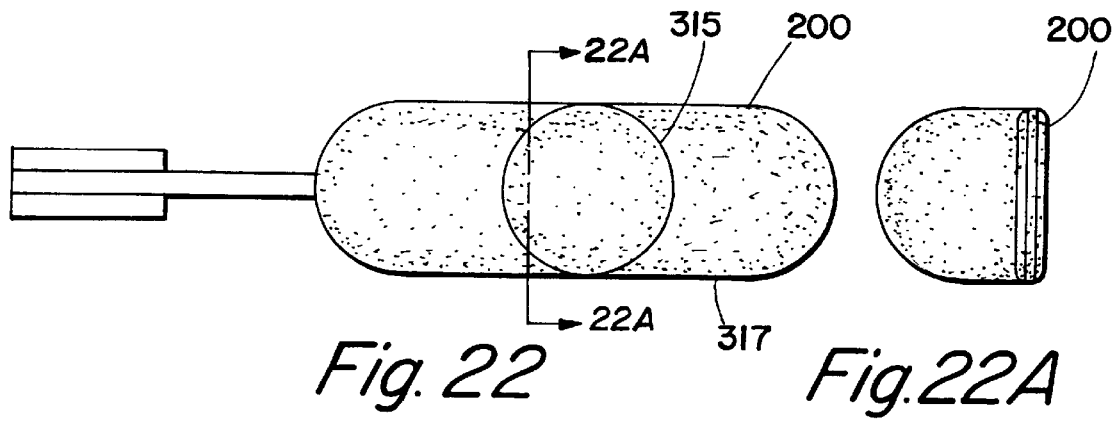
FIG. 22 is a top view of a curved or billowed snowshoe aortic diverter with a ring suspension frame.
FIG. 22A is a cross-sectional view through section A—A of the snowshoe aortic diverter depicted in FIG. 22.
Figures 23, 23A:
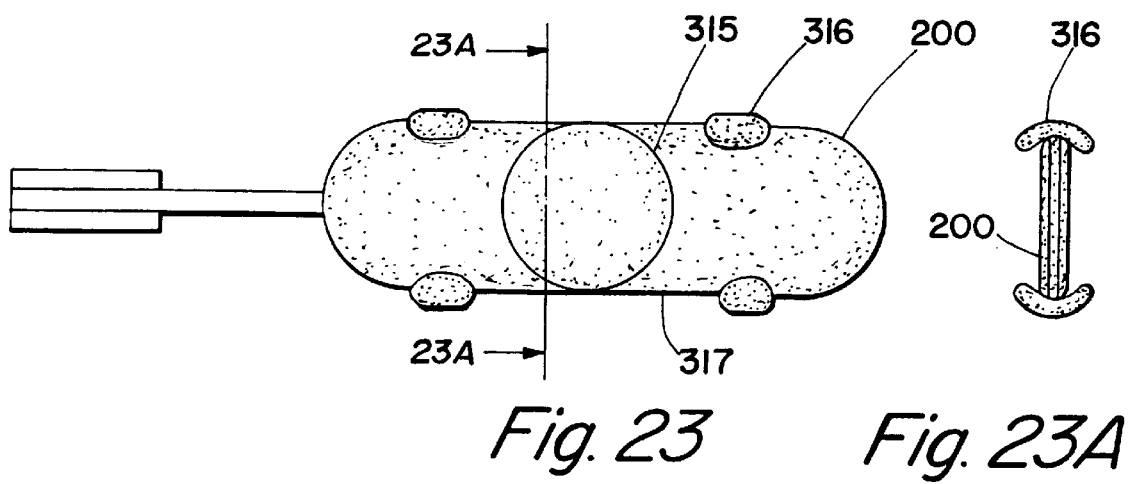
FIG. 23 is a top view of a flat snowshoe aortic diverter with supports and a ring suspension frame.
FIG. 23A is a cross-section view through section A—A of the snowshoe aortic diverter depicted in FIG. 23.

FIG. 21 shows a tapered tongue diverter 200 having suspension ring 315 mounted therein. FIG. 21A depicts an end view of the diverter of FIG. 21. Suspension ring 315 is a collapsible force biasing element which holds frame 317 in an open position when not compressed. Ring 315 is collapsible to permit loading and delivery through a standard cannula. FIG. 22 shows a snowshoe diverter with a curved or billowed membrane (see FIG. 22A cross-section), mesh, valve, or combination thereof. FIG. 23 shows a diverter having a plurality of legs 316, or external wire supports.

In another embodiment shown in FIG. 24, diverter 200 includes a flap valve formed by overlap of edges 320 of diverter 200 (see FIG. 24A cross-section). The flap valve allows blood to flow in one direction (see FIG. 24B). Thus, such a snowshoe is particularly useful for deployment below the blood cannula (see FIG. 18). Each flap of the diverter is formed of a nonporous membrane, filter mesh material, combination membrane and filter, one way flap valve, or flap valve with filter. This same design can be implemented with suspension ring 315 (see FIG. 25), multiple suspension rings (not shown), or a FIG. 8 suspension frame (see FIG. 26).

All publications and patent applications cited in this specification are herein incorporated by reference as if each individual publication or patent application were specifically and individually indicated to be incorporated by reference. While particular devices and methods have been described for diverting emboli away from the carotid arteries, once this description is known, it will be apparent to those of ordinary skill in the art that other embodiments and alternative steps are also possible without departing from the spirit and scope of the invention. Moreover, it will be apparent that certain features of each embodiment can be used in combination with devices illustrated in other embodiments. Accordingly, the above description should be construed as illustrative, and not in a limiting sense, the scope of the invention being defined by the following claims.

What is claimed is:

1. A method for protecting a patient against cerebral embolization, said method comprising the steps of:
   providing an aortic diverter comprising an elongate tube having a wall impermeable to emboli, the tube having a proximal end terminating in a substantially circular edge adapted to fill the lumen of the aorta, and a distal end, wherein the proximal and distal ends are substantially open allowing blood to enter the proximal end, flow through the tube, and exit the distal end;
   inserting the aortic diverter in the aortic arch; and
   positioning the aortic diverter so that the proximal end of the aortic diverter is upstream of the brachiocephalic trunk and the distal end of the aortic diverter is downstream of the left subclavian artery or the left brachiocephalic trunk, wherein emboli passing through the aortic arch flow through the aortic diverter and are diverted from the carotid arteries to the peripheral vasculature.

2. The method of claim 1, wherein the aortic diverter has a frustoconical shape.

3. The method of claim 1, wherein the wall of the aortic diverter is permeable to blood.

4. The method of claim 1, wherein the aortic diverter is inserted through an incision in the aortic arch.

5. The method of claim 1, wherein the aortic diverter is inserted percutaneously and advanced through the descending aorta.

6. The method of claim 1 further comprising the step of securing the aortic diverter to the lumen of the aorta.

7. A method for protecting a patient against cerebral embolization, comprising the steps of:
   providing a generally cylindrical membrane impermeable to emboli and having a first substantially circular edge and a second substantially circular edge;
   inserting the membrane into the aorta; and
   positioning the membrane in the aortic arch so that the first edge of the membrane is upstream of the brachiocephalic trunk and the second edge of the membrane is downstream of the left subclavian artery or the left brachiocephalic trunk, wherein emboli passing through the aortic arch flow through the cylindrical membrane and are diverted from the carotid arteries to the peripheral vasculature.

8. The method of claim 7, wherein the membrane has a frustoconical shape.

9. The method of claim 7, wherein the membrane is permeable to blood.

10. The method of claim 7, wherein the membrane is inserted through an incision in the aortic arch.

11. The method of claim 7, wherein the membrane is inserted percutaneously and advanced through the descending aorta.

12. The method of claim 7, further comprising the step of securing the membrane to the lumen of the aorta.

13. An aortic diverter insertable in an aorta for diverting emboli away from the carotid arteries comprising a hollow tube impermeable to emboli, said tube being curved at an angle for placement in the aortic arch and having a substantially circular proximal edge with an opening and a substantially circular distal edge with an opening.

14. The aortic diverter of claim 13, wherein the tube is a flexible windsock.

15. The aortic diverter of claim 13, wherein the tube is impermeable to blood.

16. The aortic diverter of claim 13, wherein the tube comprises a woven material.

17. The aortic diverter of claim 13, further comprising a flexible sleeve secured to the proximal edge, the sleeve being adapted to frictionally engage the lumen of the aorta.

18. The aortic diverter of claim 13, wherein the tube is expandable between a compressed condition for percutaneous delivery to the aortic arch and an expanded condition for frictional engagement with the lumen of the aorta.

19. The aortic diverter of claim 13, wherein the tube comprises a mesh material.

20. A method for protecting a patient against cerebral embolization, said method comprising the steps of:
   providing an aortic diverter comprising an elongate tube having a wall impermeable to emboli, the tube having a proximal end terminating in a substantially circular edge adapted to fill the lumen of the aorta, and a distal end, wherein the proximal and distal ends are substantially open allowing blood to enter the proximal end, flow through the tube, and exist the distal end;
   positioning the aortic diverter within the aortic arch; and
   securing the aortic diverter to the lumen of the aorta, the proximal end of the aortic diverter extending upstream of the brachiocephalic trunk.

21. The method of claim 20, wherein the aortic diverter is secured to the lumen of the aorta by frictionally engaging the lumen of the aorta.

22. The method of claim 20, wherein the aortic diverter is frictionally engaged to the lumen of the aorta by radially expanding the aortic diverter into frictional engagement to the lumen of the aorta.

23. The method of claim 20, wherein the aortic divert comprises a sleeve secured to the proximal end of the elongate tube, the sleeve being adapted to frictionally engage the lumen of the aorta, and wherein the aortic diverter is secured to the lumen of the aorta by frictionally engaging the sleeve to the lumen of the aorta.

24. The method of claim 23, wherein the sleeve is frictionally engaged by radially expanding the sleeve into frictional engagement to the lumen of the aorta.

25. The method of claim 20, wherein the aortic diverter is secured to the lumen of the aorta by suturing the aortic diverter to the lumen of the aorta.

* * * * *